(12) United States Patent
Gravley et al.

(10) Patent No.: US 9,433,917 B2
(45) Date of Patent: Sep. 6, 2016

(54) ALKYLATION UNIT AND PROCESS

(71) Applicant: UOP LLC, Des Plaines, IL (US)

(72) Inventors: Mark L. Gravley, Fort Wayne, IN (US); Martyn E. Pfile, Houston, TX (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/669,435

(22) Filed: Mar. 26, 2015

(65) Prior Publication Data
US 2015/0196894 A1    Jul. 16, 2015

Related U.S. Application Data

(62) Division of application No. 13/891,491, filed on May 10, 2013, now Pat. No. 9,000,249.

(51) Int. Cl.
| | |
|---|---|
| C07C 2/54 | (2006.01) |
| C07C 2/56 | (2006.01) |
| C07C 2/58 | (2006.01) |
| C07C 2/62 | (2006.01) |
| B01J 19/00 | (2006.01) |
| B01J 19/24 | (2006.01) |

(52) U.S. Cl.
CPC ............... *B01J 19/245* (2013.01); *C07C 2/58* (2013.01); *B01J 2219/00051* (2013.01); *B01J 2219/24* (2013.01); *C07C 2527/1206* (2013.01)

(58) Field of Classification Search
CPC ........ B01J 19/00; B01J 19/24; B01J 19/245; B01J 2219/00049; B01J 2219/00051; B01J 2219/24; C07C 2/54–2/58; C07C 2527/06; C07C 2527/08; C07C 2527/12; C07C 2527/1206; C07C 2/62
See application file for complete search history.

(56) References Cited

U.S. PATENT DOCUMENTS

| | | | | |
|---|---|---|---|---|
| 2,375,867 A | * | 5/1945 | Newman | C07C 2/62 585/251 |
| 4,179,475 A | * | 12/1979 | Makovec | C07C 2/62 585/714 |
| 7,371,918 B2 | * | 5/2008 | Gray | C07C 2/62 585/714 |
| 8,153,854 B2 | * | 4/2012 | Smith, Jr. | C07C 2/62 585/251 |

* cited by examiner

*Primary Examiner* — Natasha Young

(57) ABSTRACT

A process for producing alkylated hydrocarbons includes the steps of: (a) combining a first feed stream comprising an olefin and an isoparaffin with an alkylation catalyst stream in a first alkylation reactor, (b) removing heat of reaction from the first alkylation reactor, (c) passing an effluent of the first alkylation reactor to a first reaction zone of a second alkylation reactor operating adiabatically to thereby form a first reaction zone effluent, (d) passing the first reaction zone effluent to a second reaction zone of the second alkylation reactor for mixture with a second feed stream comprising an olefin and an isoparaffin, and (e) passing an effluent of the second alkylation reactor to a settler for separation into a hydrocarbon stream and an alkylation catalyst effluent stream. An alkylation unit for carrying out the process is also disclosed.

12 Claims, 1 Drawing Sheet

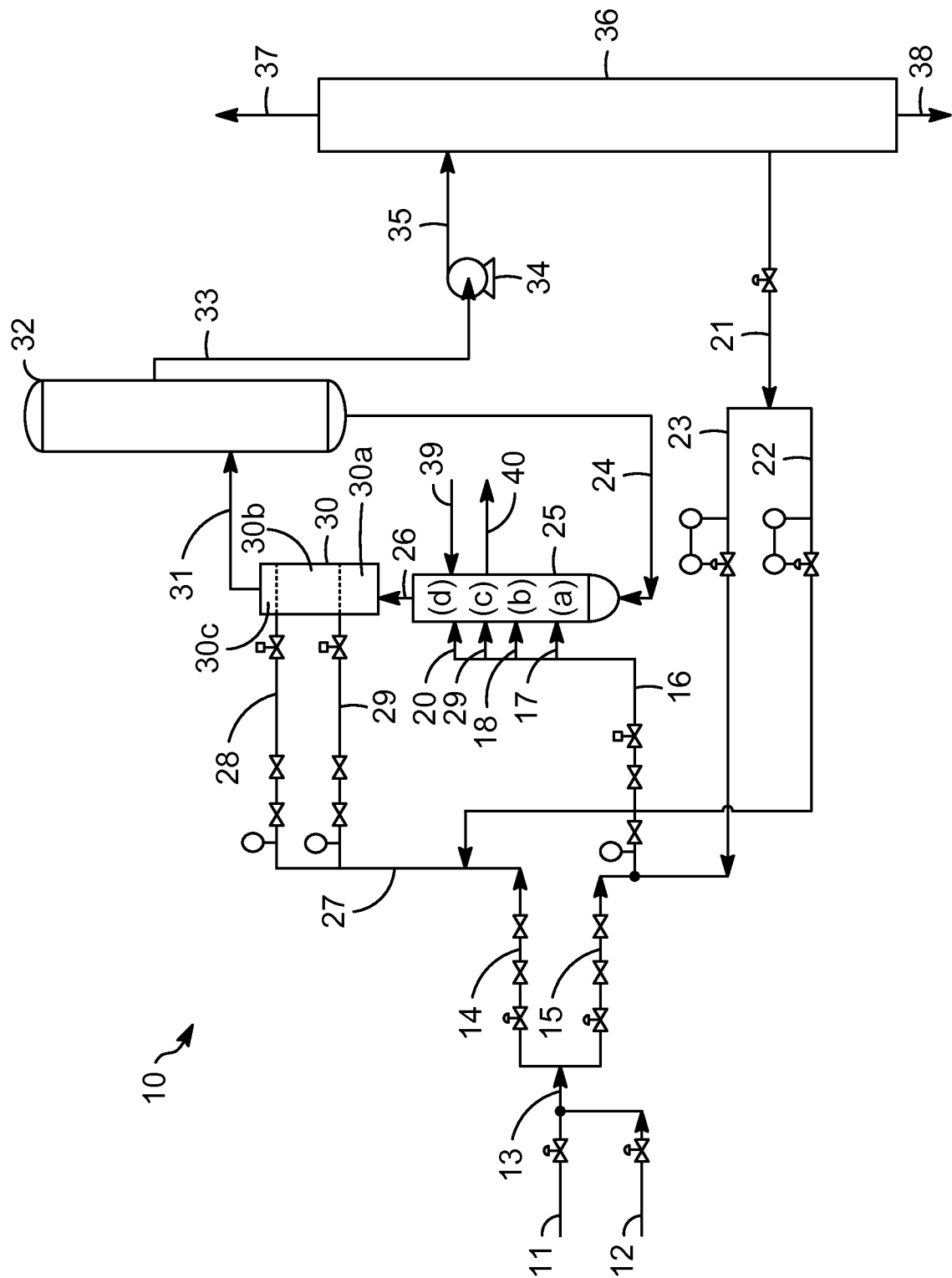

ALKYLATION UNIT AND PROCESS

CROSS-REFERENCE TO RELATED APPLICATION

This application is a Division of application Ser. No. 13/891,491, now U.S. Pat. No. 9,000,249, filed May 10, 2013, the contents of which are hereby incorporated by reference in its entirety.

BACKGROUND OF THE INVENTION

The disclosure relates to an alkylation unit and process. Generally, alkylation is a process that can be used to produce a high quality, high octane gasoline from lower boiling feeds. Usually, commercial refinery plants alkylate a feed including an isoparaffin stream, typically including isobutane, and an olefin stream, typically including one or more $C_3$-$C_5$ olefins, to form branched chain paraffin products boiling in the gasoline range, which can include hydrocarbons boiling up to about 200° C.

Increasing capacity of an alkylation unit may be implemented by various methods. The problem with increasing the capacity of an alkylation unit is that simply increasing the flow of olefin lowers the isobutane/olefin ratio, which depresses the octane number of the alkylate product, which is an undesirable result.

Therefore, what is needed is an improved alkylation unit and process that maintain the desired isobutane/olefin ratio thereby minimizing octane loss.

SUMMARY OF THE INVENTION

The foregoing needs are met by an alkylation unit including an olefin source, an isoparaffin source, a first alkylation reactor, a second alkylation reactor, and a settler. The olefin source is in fluid communication with a first isoparaffin-olefin admixture conduit and a second isoparaffin-olefin admixture conduit. The isoparaffin source is in fluid communication with the first isoparaffin-olefin admixture conduit and the second isoparaffin-olefin admixture conduit. The first alkylation reactor is in fluid communication with the first isoparaffin-olefin admixture conduit and an alkylation catalyst feed conduit supplying an alkylation catalyst. The first alkylation reactor includes a heat transfer device for removing heat of reaction from the first alkylation reactor. The second alkylation reactor has a plurality of reaction zones. A first reaction zone of the plurality of reaction zones is in fluid communication with the first alkylation reactor for receiving an effluent of the first alkylation reactor. A second reaction zone of the plurality of reaction zones is in fluid communication with the first reaction zone for receiving a first reaction zone effluent. The second reaction zone of the plurality of reaction zones is also in fluid communication with the second isoparaffin-olefin admixture conduit. The settler is in fluid communication with the second alkylation reactor, and the settler receives an effluent of the second alkylation reactor. The settler separates the effluent of the second alkylation reactor into a hydrocarbon stream and an alkylation catalyst effluent stream. Preferably, the isoparaffin source comprises a $C_4$-$C_5$ alkane and the olefin source comprises a $C_3$-$C_5$ alkene. Preferably, the second alkylation reactor is operated adiabatically.

The alkylation unit can further include a fractionation unit in fluid communication with the settler. The fractionation unit receives the hydrocarbon stream from the settler and separates the hydrocarbon stream into an alkylate stream and an isoparaffin recycle stream in fluid communication with the first and second isoparaffin-olefin admixture conduit.

In one version of the alkylation unit, a ratio of isoparaffin to olefin in terms of total flow rate in the first isoparaffin-olefin admixture conduit and the second isoparaffin-olefin admixture conduit is about 3:1 and about 1:3. A molar ratio of isoparaffin to olefin in the first isoparaffin-olefin admixture conduit and the second isoparaffin-olefin admixture conduit can be between about 5:1 and about 20:1. A volume ratio of the alkylation catalyst to a first feed stream in the first isoparaffin-olefin admixture conduit can be between about 1:1 and about 4:1.

In one version of the alkylation unit, the first isoparaffin-olefin admixture conduit is in fluid communication with the first alkylation reactor via a plurality of inlet loci comprising four to eight inlet points longitudinally spaced intermediate ends of the first alkylation reactor. In one version of the alkylation unit, the settler is in fluid communication with the first alkylation reactor, and the first alkylation reactor receives the alkylation catalyst effluent stream. In one version of the alkylation unit, the second isoparaffin-olefin admixture conduit is in fluid communication with a third isoparaffin-olefin admixture conduit, and a third reaction zone of the plurality of reaction zones of the second alkylation reactor is in fluid communication with the second reaction zone for receiving a second reaction zone effluent wherein the third reaction zone is also in fluid communication with the third isoparaffin-olefin admixture conduit.

The foregoing needs are also met by a process for producing alkylated hydrocarbons. The process comprising includes the steps of (a) combining a first feed stream comprising an olefin and an isoparaffin with an alkylation catalyst stream in a first alkylation reactor; (b) removing heat of reaction from the first alkylation reactor; (c) passing an effluent of the first alkylation reactor to a first reaction zone of a second alkylation reactor to thereby form a first reaction zone effluent; (d) passing the first reaction zone effluent to a second reaction zone of the second alkylation reactor for mixture with a second feed stream comprising an olefin and an isoparaffin; and (e) passing an effluent of the second alkylation reactor to a settler for separation into a hydrocarbon stream and an alkylation catalyst effluent stream. Preferably, the isoparaffin comprises a $C_4$-$C_5$ alkane, and the olefin comprises a $C_3$-$C_5$ alkene. The second alkylation reactor can be operated adiabatically.

The process can further include the steps of (f) passing the hydrocarbon stream to a fractionation unit, (g) separating the hydrocarbon stream into an alkylate stream and an isoparaffin recycle stream, and (h) combining the isoparaffin recycle stream with the first feed stream and the second feed stream. The process can further include the step of controlling a ratio of a first volumetric flow rate of the first feed stream to a second volumetric flow rate of the second feed stream to be between about 3:1 and about 1:3. The process can further include the step of directing the first feed stream into the first alkylation reactor through a plurality of inlet loci comprising four to eight inlet points longitudinally spaced intermediate ends of the first alkylation reactor. The process can further include the step of passing the alkylation catalyst effluent stream from the settler to the first alkylation reactor. The process can further include the step of passing a second reaction zone effluent to a third reaction zone of the second alkylation reactor for mixture with a third feed stream comprising an olefin and an isoparaffin.

The process can further include the steps of controlling a first molar ratio of isoparaffin to olefin in the first feed stream to be between about 5:1 and about 20:1, and controlling a second molar ratio of isoparaffin to olefin in the second feed stream to be between about 5:1 and about 20:1. The process can further include the step of controlling a volume ratio of the alkylation catalyst to the first feed stream to be between about 1:1 and about 4:1.

It is therefore an advantage of the invention to provide an improved alkylation unit and process that achieve an increase in unit capacity while at the same time minimizing octane loss.

These and other features, aspects, and advantages of the present invention will become better understood upon consideration of the following detailed description, drawings and appended claims.

BRIEF DESCRIPTION OF THE DRAWING

The FIGURE is a schematic process flow diagram of an alkylation unit according to the invention.

DETAILED DESCRIPTION OF THE INVENTION

As used herein, the hydrocarbon molecules may be abbreviated $C_1, C_2, C_3 \ldots C_n$ where "n" represents the number of carbon atoms in the one or more hydrocarbon molecules. Additionally, characterizing a stream as, e.g., an "olefin stream" can mean a stream including or rich in at least one olefin.

As used herein, the term "unit" or "system" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "rich" can mean an amount of at least generally about 30%, preferably about 50%, and optimally about 70%, by mole, of a compound or class of compounds in a feed, an effluent, or a stream.

As used herein, the term "substantially" can mean an amount of at least generally about 80%, preferably about 90%, and optimally about 99%, by mole, of a compound or class of compounds in a feed, an effluent, or a stream.

As used herein, the term "vapor" can mean a gas or a dispersion that may include or consist of one or more hydrocarbons.

As used herein, hydrofluoric acid can disassociate and may form ions of $H_3O^+$, $H^+$, $FHF^-$, and $F^-$.

The term "communication" means that material flow is operatively permitted between enumerated components.

As depicted, process flow lines in the FIGURE can be referred to as lines, conduits, feeds, effluents, or streams. Particularly, a line or a conduit can contain one or more feeds, effluents, or streams, and one or more feeds, effluents, and streams can be contained by a line or a conduit.

Referring to the FIGURE, an acid alkylation unit or system 10 can include a first alkylation reactor 25, preferably a cooler-reactor, and a second alkylation reactor 30, preferably a multi-zone reactor arranged in series for the purposes of carrying out an alkylation reaction.

Usually, the alkylation reaction can include the reaction of an isoparaffin, such as isobutane, with an olefin such as propylene, isobutylene, 1-butene, 2-butene, and pentenes. Generally, the reaction of an isoparaffin with a $C_3$ or a $C_4$ olefin, such as isobutylene, 1-butene, and/or 2-butene, is an example of a preferred reaction involving these specified materials and mixture. One preferred mixture is an isoparaffin and typically a mixed "butene" produced from a catalytic cracking operation, which can include about 25%, by volume, of 1-butene, about 30%, by volume, of isobutylene and about 45%, by volume, of 2-butene. Usually, the stream rich in isobutane can at least be partially provided by recycling isobutane from a downstream fractionation zone and include make-up isobutane from refinery or chemical manufacturing units. The recycle isobutane provides a molar excess of isoparaffin as described below.

Typically, the alkylation catalyst can include a hydrofluoric acid, a sulfuric acid, a phosphoric acid, a metal halide, or other suitable alkylation catalyst. Preferably, the catalyst is a hydrofluoric acid. Furthermore, the catalyst may be substantially anhydrous hydrogen fluoride containing various additives or promoters such as boron trifluoride. Ordinarily, commercially available anhydrous hydrogen fluoride will be charged to the alkylation system as fresh catalyst. It is however, possible to use hydrogen fluoride containing as much as about 2.5% water by weight.

Generally, the alkylation reaction is carried out with substantial molar excess of isoparaffin:olefin, typically in excess of about 1:1, usually about 4:1 to about 70:1, preferably about 5:1 to about 20:1, more preferably about 7:1 to about 15:1.

Usually, the system or unit 10 can maintain an acid:hydrocarbon volume ratio of 1:1 to 4:1, with one preferred range of 2:1 to 3:1. Another preferred range for the acid:hydrocarbon volume ratio is not lower than about 2.5:1. The acid:hydrocarbon volume ratio will be higher in the first reactor 25, and the acid:hydrocarbon volume ratio depends on how the feed and recycle isobutane are split between the two reactors. The acid:hydrocarbon volume ratio in second reactor 30 will be the overall ratio, so in the preferred range.

The pressure in the reactors has to be at least high enough to keep the hydrocarbon in the liquid phase. The minimum pressure is about 600 kPa, though this depends on the temperature in the reactor and settler. The temperature range can be 15° C. to 50° C. with a preferred range of about 25° C. to 40° C. Preferred pressure in the settler is about 600 kPa to 850 kPa.

Olefin hydrocarbon via line 11 is premixed with an isoparaffin make-up stream 12 to form a first isoparaffin-olefin admixture stream 13. Typically, at least a portion 14 of the stream 13 may be bypassed around the cooler-reactor 25. Typically, at least about 25% to about 75%, by volume, optimally about 50%, by volume, of the stream 13 can be bypassed as the portion 14. The remainder can pass as a stream 15 to the cooler-reactor 25. A stream 23, including one or more isoparaffins, typically isobutane, can be combined with the stream 15. Usually, the stream 23, including one or more isoparaffins, can include isoparaffins obtained from a recycled stream 21 from downstream fractionation unit 36. The combined streams 15 and 23 can form a hydrocarbon feed 16. This hydrocarbon feed 16 can be split into several streams, namely stream 17, stream 18, stream 19, and stream 20 before entering the cooler-reactor 25 at inlet loci (a), (b), (c) and (d). Inlet loci (a), (b), (c) and (d) may be, for example, spray nozzles and the like. Thus, the vertically spaced streams 17, 18, 19, and 20 may ensure good dispersion of the hydrocarbons through an acid phase in the cooler-reactor 25.

As described above with reference to the preferred embodiment, the purpose of a plurality of inlet loci is to inject the feed mixture into a cooling section of the reactor cooler through the alkylation catalyst phase already present in the cooler-reactor 25 in such a manner that the evolved heat of reaction may be removed almost immediately by a heat exchanger using coolant, such as relatively cold water, flowing through the heat exchange lines 39 and 40. Typically, the heat exchanger is a conventional heat exchanger using tubes for the passage of the coolant with the reaction taking place on the shell side of the heat exchanger. By operation in this manner, the alkylation reaction takes place in the immediate vicinity of the heat removal so that regulated isothermal conditions are maintained in reaction cooler 25.

The hydrocarbon and alkylation catalyst may react within the cooler-reactor 25 to provide a cooler-reactor effluent 26. The effluent 26 can enter the multi-zone alkylation reactor 30 with a first reaction zone 30a, a second reaction zone 30b and, optionally, a third reaction zone 30c. Such first reaction zone 30a, second reaction zone 30b and third reaction zone 30c are operably related to each other such that a first reaction zone effluent passes to a second reaction zone 30b from the first reaction zone 30a and a second reaction zone effluent passes to a third reaction zone 30c from the second reaction zone 30b. The cooler reactor effluent 26 enters the multi-zone alkylation reactor 30 at the first reaction zone 30a. Cooler-reactor bypass stream 14 can be combined with the remaining portion 22 of isoparaffin recycle stream 21 resulting in stream 27. A portion of the second isoparaffin-olefin admixture stream 27 may enter the multi-zone reactor 30 via line 29 at reaction zone 30b. Optionally, the remainder of stream 27 may pass as stream 28 to the multi-zone reactor at reaction zone 30c.

The ratio of isobutane to olefin is calculated for various streams. This ratio is calculated by taking the flow rate of isobutane in a particular stream and dividing by the flow rate of the total olefins in that same stream. The ratio can be calculated on either a volumetric or a molar basis. Preferably, the ratio (on a volumetric basis) of isobutane to olefin in stream 16 is in the range of 7 to 12, the ratio for stream 27 is in the range of 5 to 10, and the ratio for combined streams 13 and 21 is in the range of 7 to 15.

In one embodiment of the invention, the multi-zone reactor is operated adiabatically. Therefore, the multi-zone reactor is dissimilar to the cooler-reactor in that that the evolved heat of reaction is not removed by heat exchange.

The hydrocarbons and alkylation catalyst may react within the multi-zone reactor 30 to provide a multi-zone reactor effluent 31. The multi-zone reactor 30 overcomes the reducing of octane caused by a lower isoparaffin-olefin ratio by increasing the localized isoparaffin-olefin ratio using unreacted isobutane from the cooler-reactor 25 contained in stream 26 in subsequent multi-zone reactor 30.

The multi-zone reactor effluent 31 can enter acid settler 32. Generally, the acid settler 32 can allow the second reactor effluent 31 to split into three phases, namely, a vapor phase, a hydrocarbon phase, and an alkylation catalyst or acid phase. The hydrocarbon phase can be drawn through a stream 33, passed through the fluid transfer device 34, and provided to downstream fractionation unit 36 via stream 35 for recovering the alkylate product 38, isoparaffins 21 and other hydrocarbons 37 such as propane. The acid phase can be provided via a stream 24 to the cooler-reactor 25. The acid phase in stream 24 can be combined with additional make-up acid, and the combination can flow to the cooler-reactor 25. The acid phase in stream 24 can be supplied to a regeneration zone for regenerating the alkylation catalyst. The regenerated acid catalyst can be returned via a stream to the cooler reactor 25, although the regenerated catalyst can be provided to other locations within the system 10.

Generally, the embodiments provided herein can provide a method of expanding capacity of an alkylation unit, such as a hydrogen fluoride alkylation unit, by adding a second reactor in series with a first reactor wherein the first reactor is preferably a cooler-reactor 25 and the second reactor is preferably a multi-zone reactor 30 operating adiabatically.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

The invention claimed is:

1. An alkylation unit comprising:
   an olefin source in fluid communication with a first isoparaffin-olefin admixture conduit and a second isoparaffin-olefin admixture conduit;
   an isoparaffin source in fluid communication with the first isoparaffin-olefin admixture conduit and the second isoparaffin-olefin admixture conduit;
   a first alkylation reactor in fluid communication with the first isoparaffin-olefin admixture conduit and an alkylation catalyst feed conduit supplying an alkylation catalyst, the first alkylation reactor including a heat transfer device for removing heat of reaction from the first alkylation reactor;
   a second alkylation reactor having a plurality of reaction zones, a first reaction zone of the plurality of reaction zones being in fluid communication with the first alkylation reactor for receiving an effluent of the first alkylation reactor, a second reaction zone of the plurality of reaction zones being in fluid communication with the first reaction zone for receiving a first reaction zone effluent, the second reaction zone of the plurality of reaction zones also being in fluid communication with the second isoparaffin-olefin admixture conduit; and
   a settler in fluid communication with the second alkylation reactor, the settler receiving an effluent of the second alkylation reactor, the settler separating the effluent of the second alkylation reactor into a hydrocarbon stream and an alkylation catalyst effluent stream.

2. The alkylation unit of claim 1 further comprising a fractionation unit in fluid communication with the settler, the fractionation unit receiving the hydrocarbon stream from the settler and separating the hydrocarbon stream into an alkylate stream and an isoparaffin recycle stream in fluid communication with the first and second isoparaffin-olefin admixture conduit.

3. The alkylation unit of claim 1 wherein a ratio of isoparaffin to olefin in terms of total flow rate in the first isoparaffin-olefin admixture conduit and the second isoparaffin-olefin admixture conduit is about 3:1 and about 1:3.

4. The alkylation unit of claim 1 wherein the first isoparaffin-olefin admixture conduit is in fluid communication with the first alkylation reactor via a plurality of inlet loci comprising four to eight inlet points longitudinally spaced intermediate ends of the first alkylation reactor.

5. The alkylation unit of claim 1, wherein the isoparaffin source comprises a $C_4$-$C_5$ alkane and the olefin source comprises a $C_3$-$C_5$ alkene.

6. The alkylation unit of claim 1 wherein the settler is in fluid communication with the first alkylation reactor, the first alkylation reactor receiving the alkylation catalyst effluent stream.

7. The alkylation unit of claim 1 wherein the second alkylation reactor is operated adiabatically.

8. The alkylation unit of claim 1 wherein the second isoparaffin-olefin admixture conduit is in fluid communication with a third isoparaffin-olefin admixture conduit; and a third reaction zone of the plurality of reaction zones of the second alkylation reactor is in fluid communication with the second reaction zone for receiving a second reaction zone effluent, the third reaction zone also being in fluid communication with the third isoparaffin-olefin admixture conduit.

9. The alkylation unit of claim 1 wherein a molar ratio of isoparaffin to olefin in the first isoparaffin-olefin admixture conduit and the second isoparaffin-olefin admixture conduit is between about 5:1 and about 20:1.

10. The alkylation unit of claim 1 wherein a volume ratio of the alkylation catalyst to a first feed stream in the first isoparaffin-olefin admixture conduit is between about 1:1 and about 4:1.

11. An alkylation unit comprising:
an olefin source in fluid communication with a first isoparaffin-olefin admixture conduit and a second isoparaffin-olefin admixture conduit;
an isoparaffin source in fluid communication with the first isoparaffin-olefin admixture conduit and the second isoparaffin-olefin admixture conduit;
a first alkylation reactor in fluid communication with the first isoparaffin-olefin admixture conduit and an alkylation catalyst feed conduit supplying an alkylation catalyst, the first alkylation reactor including a heat transfer device for removing heat of reaction from the first alkylation reactor, wherein the first isoparaffin-olefin admixture conduit is in fluid communication with the first alkylation reactor via a plurality of inlet loci comprising four to eight inlet points longitudinally spaced intermediate ends of the first alkylation reactor;
a second alkylation reactor having a plurality of reaction zones, a first reaction zone of the plurality of reaction zones being in fluid communication with the first alkylation reactor for receiving an effluent of the first alkylation reactor, a second reaction zone of the plurality of reaction zones being in fluid communication with the first reaction zone for receiving a first reaction zone effluent, the second reaction zone of the plurality of reaction zones also being in fluid communication with the second isoparaffin-olefin admixture conduit; and
a settler in fluid communication with the second alkylation reactor, the settler receiving an effluent of the second alkylation reactor, the settler separating the effluent of the second alkylation reactor into a hydrocarbon stream and an alkylation catalyst effluent stream.

12. The alkylation unit of claim 11 further comprising a fractionation unit in fluid communication with the settler, the fractionation unit receiving the hydrocarbon stream from the settler and separating the hydrocarbon stream into an alkylate stream and an isoparaffin recycle stream in fluid communication with the first and second isoparaffin-olefin admixture conduit.

* * * * *